United States Patent
Takino et al.

(10) Patent No.: US 8,157,781 B2
(45) Date of Patent: Apr. 17, 2012

(54) DISPOSABLE BODY WASTE HANDLING ARTICLE

(75) Inventors: Shunsuke Takino, Kagawa-ken (JP);
Yuki Maeda, Kagawa-ken (JP);
Hiroyuki Tanji, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 813 days.

(21) Appl. No.: 11/764,857

(22) Filed: Jun. 19, 2007

(65) Prior Publication Data

US 2007/0299414 A1  Dec. 27, 2007

(30) Foreign Application Priority Data

Jun. 23, 2006  (JP) .................................. 2006-174443

(51) Int. Cl.
*A61F 13/15* (2006.01)
*A61F 13/20* (2006.01)
(52) U.S. Cl. .......... 604/385.27; 604/385.24; 604/385.28
(58) Field of Classification Search ............. 604/385.19, 604/385.27, 385.24, 385.28
See application file for complete search history.

(56) References Cited

U.S. PATENT DOCUMENTS

| 6,443,933 | B1 * | 9/2002 | Suzuki et al. | 604/385.04 |
| 2004/0064124 | A1 * | 4/2004 | Kawata et al. | 604/385.03 |
| 2004/0133178 | A1 | 7/2004 | Otsubo et al. | |
| 2005/0177125 | A1 * | 8/2005 | Kondo | 604/385.29 |
| 2005/0245158 | A1 * | 11/2005 | Yahiaoui et al. | 442/118 |

FOREIGN PATENT DOCUMENTS

| JP | 2000-042033 | 2/2000 |
| JP | 2001-513669 | 9/2001 |
| JP | 3510150 | 1/2004 |
| JP | 2004-248853 A | 9/2004 |

* cited by examiner

*Primary Examiner* — Melanie Hand
(74) *Attorney, Agent, or Firm* — Lowe, Hauptman, Ham & Berner, LLP

(57) ABSTRACT

A body waste handling article includes a first sheet, a second sheet and a body fluid absorbent core sandwiched between these two sheets, wherein the first sheet defines a liquid-pervious skin-contacting surface. The second sheet is rectangular and has a pair of ends and a pair of lateral edges wherein inside these ends and lateral edges, end flaps and lateral flaps are formed. The end flaps and the lateral flaps are provided with elastic members attached in a stretched state thereto so as to extend along the ends and the lateral edges and to become contiguous one to another at corners of the second sheet.

4 Claims, 10 Drawing Sheets ical problems of prior art as have
DISPOSABLE BODY WASTE HANDLING ARTICLE

RELATED APPLICATIONS

The present application is based on, and claims priority from, Japan Application Number 2006-174443, filed Jun. 23, 2006, the disclosure of which is hereby incorporated by reference herein in its entirety.

BACKGROUND OF THE INVENTION

The present invention relates generally to a disposable article suitable to handle body waste such as feces and urine.

There have already been proposed body waste handling articles each comprising a panel formed by a wrapping body fluid absorbent material such as fluff pulp with a liquid-pervious sheet, a leak-barrier peripheral wall provided along a peripheral edge of the panel so as to define a space for receiving body waste, an opening communicating with the space provided in the leak-barrier peripheral wall and elastic members attached in a stretched state to the leak-barrier peripheral wall so as to surround the opening.

For example, in a disposable body fluid handling article disclosed in Japanese Unexamined Patent Application Publication No. 2000-42033 (hereinafter referred to as "Reference 1"), a body fluid absorbent structure comprising a liquid-pervious topsheet, a liquid-impervious backsheet and a liquid-absorbent core sandwiched between these two sheets is provided along a peripheral edge thereof with a leak-barrier cover sheet so as to cover the body fluid absorbent structure from above so that the body fluid absorbent structure cooperates with the cover sheet to for a space for receiving body waste. The cover sheet defines an opening allowing body waste to flow into the space and the opening is provided along its peripheral edge with elastic member attached in a stretched state thereto.

Japanese Patent Publication No. 3510150 (hereinafter referred to as "Reference 2") discloses a disposable body waste handling article. The body waste handling article disclosed therein comprises a rectangular body fluid absorbent panel and strip-like leak-barrier sheets serving as leak-barrier walls provided along four sides of the rectangular body fluid absorbent panel, respectively, so that the panel cooperates with these leak-barrier walls to define a space receiving body waste. These leak-barrier walls define also an opening communicating with the space. The leak-barrier walls are provided along a peripheral edge of the opening with elastic members.

National Publication of Translated Version No. 2001-513669 (hereinafter referred to as "Reference 3") discloses an absorbent article such as a diaper or an incontinence guard. In this absorbent article, absorbent material is sandwiched between a liquid-pervious sheet and a liquid-impervious sheet to form a panel-shaped article. In the panel-shaped article, the liquid-pervious sheet is covered with a topsheet formed with an oval opening. Between these liquid-pervious sheet and the topsheet, a space for receiving body waste is defined so that body waste the may flow through the opening of the topsheet into the space. The topsheet is provided along a peripheral edge of the opening with an elastic member.

In the case of the body waste handling article disclosed in Reference 1, the trapezoidal or rectangular panel comprising the topsheet, the backsheet and the core sandwiched between these two sheets must be folded back in two along a center line bisecting a width of the panel and then the peripheral edge must be put flat and bonded together. A process for making this body waste handling article thus includes an additional step of folding the panel back onto itself and bonding the peripheral edge to itself. Such process is disadvantageously complex.

For the body waste handling article disclosed in Reference 2, the strip-like leak-barrier sheets prepared separately of the panel must be attached to the respective sides of the rectangular panel and, in addition, these leak-barrier sheets must be previously provided with the elastic members attached in a stretched state thereto. The construction of the body waste handling article is complicated and the number of parts is correspondingly increased, leading to a cost of manufacturing increased.

The absorbent article disclosed in Reference 3 requires the topsheet, the material to be prepared separately of the panel-shaped article and a cost of manufacturing is correspondingly increased.

SUMMARY OF THE INVENTION

To overcome the technical problems of prior art as have been described above, it is an object of the present invention to provide a disposable body waste handling article with a simplified construction.

The object set forth above is achieved, according to the present invention, by an improvement in a disposable body waste handling article comprising a first sheet, a second sheet and a body fluid absorbent core wherein the first sheet defines a liquid-pervious skin-contactable surface.

The improvement according to the present invention is in that the second sheet is shaped in a rectangle extending outward beyond a peripheral edge of the core and contoured by a pair of lateral edges extending in parallel to each other in a longitudinal direction and a pair of ends extending in parallel to each other in a transverse direction, the second sheet defining lateral flaps inside the respective lateral edges thereof and defining end flaps inside the respective ends thereof, the lateral flaps and the end flaps being provided along the lateral edges and the ends with elastic members attached in a stretched state to the lateral flaps and the end flaps so that these elastic members overlap one upon another and cooperate one with another to form a rectangular loop, contraction of the elastic members constrict the lateral flaps and the end flaps in the longitudinal direction as well as in the transverse direction so as to narrow the loop and causes the lateral flaps and the end flaps to be folded back along the peripheral edge of the core with the skin-contactable surface inside.

According to one preferred embodiment of the present invention, the elastic members comprise a first elastic member continuously extending along a pair of the lateral edges and one of the ends and a second elastic member extending along the other of the ends in a manner that these first and second elastic members are overlapped one upon another at corners of the rectangle and thereby substantially contiguous one to another.

According to another preferred embodiment of the present invention, the elastic members comprise a third elastic member continuously extending along one of the lateral edges and a pair of the ends and a fourth elastic member extending along the other of the lateral edges in a manner that these third and fourth elastic members are overlapped one upon another at corners of the rectangle and thereby substantially contiguous one to another.

According to still another preferred embodiment of the present invention, the second sheet has inner side facing the core and outer side facing away from the core and adapted to be attached to an inner surface of a diaper or a diaper cover in a crotch region thereof.

According to yet another preferred embodiment of the present invention, the second sheet is liquid-impervious.

According to further another preferred embodiment of the present invention, a liquid-impervious leak-barrier sheet is sandwiched between the core and the second sheet.

According to an additional preferred embodiment of the present invention, the article is attached, in a vicinity of the end flaps thereof, to a belt-like member defining an annulus which is elastically stretchable and contractible in a circumferential direction so that the article cooperates with the belt-like member to form a pants-type wearing article.

According to the present invention, the rectangular second sheet is provided along the lateral edges and the ends thereof with the elastic members attached in a stretched state thereto so that contraction of these elastic members constricts the lateral flaps as well as the end flaps and thereby narrows the loop defined by these flaps. Constriction of these flaps forms the leak-barrier peripheral walls and an opening surrounded by these leak-barrier peripheral walls adapted to receive body waste such as feces and urine. In this way, a three-dimensional body waste handling article can be obtained from a simple planar construction.

Both in the handling article according to the embodiment wherein the elastic members comprise the first elastic member extending along a pair of the lateral edges and one of the ends in the second sheet and in the handling article according to the embodiment wherein the elastic members comprise the third elastic member extending along one of the lateral edges and a pair of the ends, the rectangular loop can be formed by paired elastic member.

The outer side of the handling article may be adapted to be attached to diaper or diaper cover to facilitate the handling article to be put on the wearer's body.

When the liquid-impervious sheet is used as the second sheet of the handling article, the handling article may be combined with cloth pants to use the handling article as the wearing article for incontinent patient.

The handling article according to the present invention may be attached, in the vicinity of the end flaps thereof, to an annular belt-like member to obtain a pants-type wearing article.

DETAILED DESCRIPTION OF THE PREFERRED EMBODIMENTS

Details of a disposable body waste handling article according to the present invention will be more fully understood from the description given hereunder with reference to the accompanying drawings.

Figure 1:
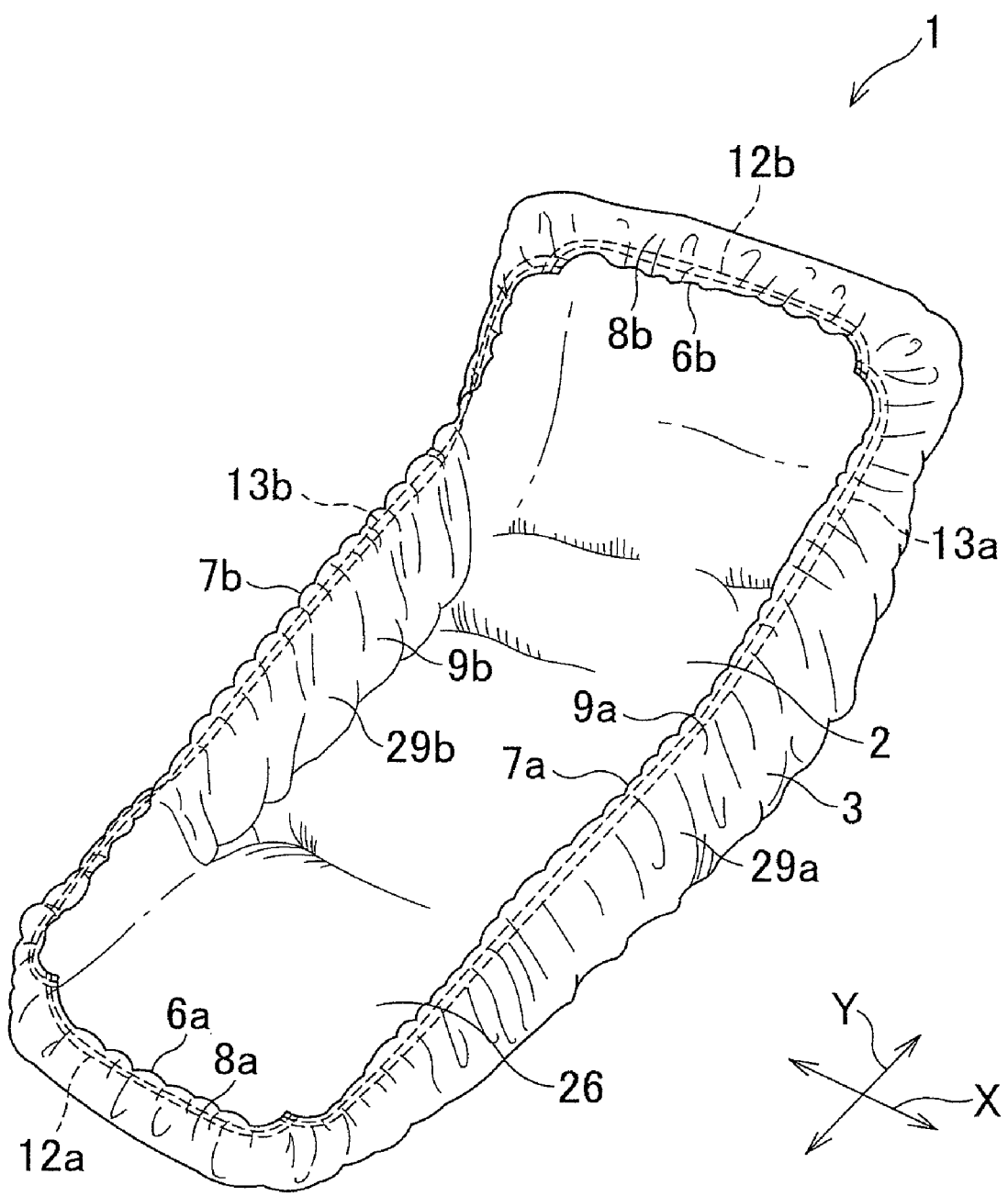
FIG. 1 is a perspective view of a body waste handling article.

FIG. 1 is a perspective view of a disposable body waste handling article 1. The handling article 1 has a transverse direction X and a longitudinal direction Y which are orthogonal to each other. The handling article 1 has also a skin-contactable inner surface and an outer surface lying on the opposite side of the inner surface wherein the inner surface is defined by a liquid-pervious topsheet 2 referred to as a first sheet according to the present invention and the outer sheet is defined by one of a liquid-pervious and liquid-impervious backsheet 3 referred to as a second sheet according to the present invention. The handling article 1 further has a pair of ends 6*a*, 6*b* substantially extending in parallel to each other in the transverse direction X and a pair of lateral edges 7*a*, 7*b* substantially extending in parallel to each other in the longitudinal direction Y. Inside the respective ends 6*a*, 6*b* and the respective lateral edges 7*a*, 7*b*, the topsheet 2 and the backsheet 3 placed upon each other so as to form flexible end flaps 8*a*, 8*b* and lateral flaps 9*a*, 9*b*. The respective end flaps 8*a*, 8*b* are provided with elastic members 12*a*, 12*b* attached in a stretched state thereto so as to extend along the respective ends 6*a*, 6*b* and the respective lateral flaps 9*a*, 9*b* are provided with elastic members 13*a*, 13*b* attached in a stretched state thereto so as to extend along the respective lateral edges 13*a*, 13*b*. Referring to FIG. 1, the elastic member 12*a* is similar in tension to the elastic member 12*b* while the elastic member 13*a* is similar in tension to the elastic member 13*b* so that the handling article 1 is curved in the longitudinal direction Y as well as in the transverse direction X with the topsheet 2 inside under contraction of these elastic members 12*a*, 12*b*, 13*a*, 13*b*. For the handling article 1 curved in this manner, the end flaps 8*a*, 8*b* and the lateral flaps 9*a*, 9*b* cooperate together so as to define peripheral walls of the handling article 1. It should be noted that such curvature of the handling article 1 as seen in FIG. 1 is relatively significant in the longitudinal direction Y and not so significant in the transverse direction X.

Figure 2:
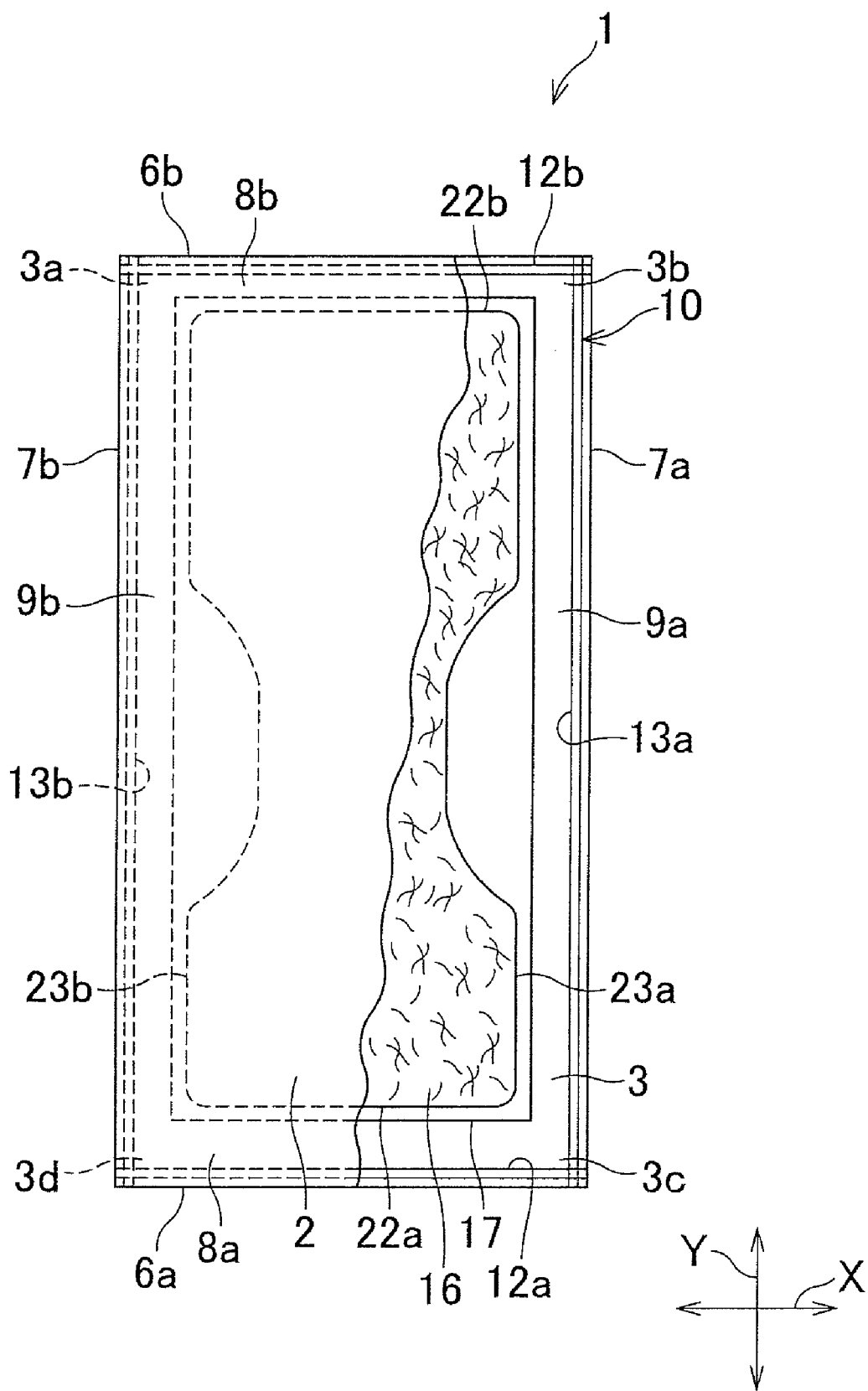
FIG. 2 is a partially cutaway plan view of the body waste handling article.

FIG. 2 is a partially cutaway plan view showing the handling article 1 as the respective elastic members 12*a*, 12*b*, 13*a*, 13*b* are stretched from the state as shown in FIG. 1 in the longitudinal direction Y and in the transverse direction X, respectively. The handling article 1 flattened in this manner includes a body fluid absorbent core 16 sandwiched between the topsheet 2 and the backsheet 3 both being rectangular in such flattened state and a leak-barrier sheet 17 made of a liquid-impervious plastic film sandwiched between the core 16 and the backsheet 3. The core 16 has a width reduced in the middle as viewed in the longitudinal direction Y so that the core 16 has an hourglass-shape as a whole. The leak-barrier sheet 17 is preferably dimensioned to extend outward beyond a peripheral edge of the core 16. The topsheet 2 and the backsheet 3 extend outward beyond the peripheral edge of the core 16 and are then put flat and bonded together by means of suitable adhesive or sealing technique so as to form the end flaps 8*a*, 8*b* extending along ends 22*a*, 22*b* of the core 16 and the lateral flaps 9a, 9b extending along lateral edges 23a, 23b of the core 16. These flaps 8a, 8b, 9a, 9b are respectively provided with a pair of the elastic members 12a, a pair of the elastic members 12b, a pair of the elastic members 13a and a pair of the elastic members 13b sandwiched between the topsheet 2 and the backsheet 3 and bonded in a stretched state to at least one of these two sheets 2, 3, for example, to the backsheet 3 by means of hot melt adhesive (not shown). In this way, the flaps 8a, 8b, 9a, 9b are elasticized. These elastic members 12a, 12b, 13a, 13b overlap one another at corners 3a, 3b, 3c, 3d of the backsheet 3 so as to be substantially contiguous one to another and thereby to form a rectangular loop 10 as a whole.

When the handling article 1 arranged as shown in FIG. 2 is free, the rectangular loop is constricted as the respective elastic members 12a, 12b, 13a, 13b contract. Thereupon, the end flaps 8a, 8b are gathered in the transverse direction X and folded back with the topsheet 2 inside while the lateral edges 9a, 9b are gathered in the longitudinal direction Y and folded back with the topsheet 2 inside. Portions of the respective flaps extending along the ends 22a, 22b and the lateral edges 23a, 23b of the core 16 having a stiffness higher than that of these flaps function as proximal ends and edges along which these flaps are folded back. The core 16 itself also is appropriately curved in the transverse direction X as well as in the longitudinal direction Y to facilitate the handling article 1 as a whole to change its shape from a planar shape to a three-dimensional shape as shown in FIG. 1. It should be understood that the flaps 8a, 8b, 9a, 9b may sometimes be folded back not with the topsheet 2 inside but with the backsheet 3 inside as the elastic members 12a, 12b, 13a, 13b contract. In this case, these flaps 8a, 8b, 9a, 9b may be guided so as to be folded back with the topsheet 2 inside as shown by FIG. 1 by putting the hands on the handling article 1.

Figure 3:
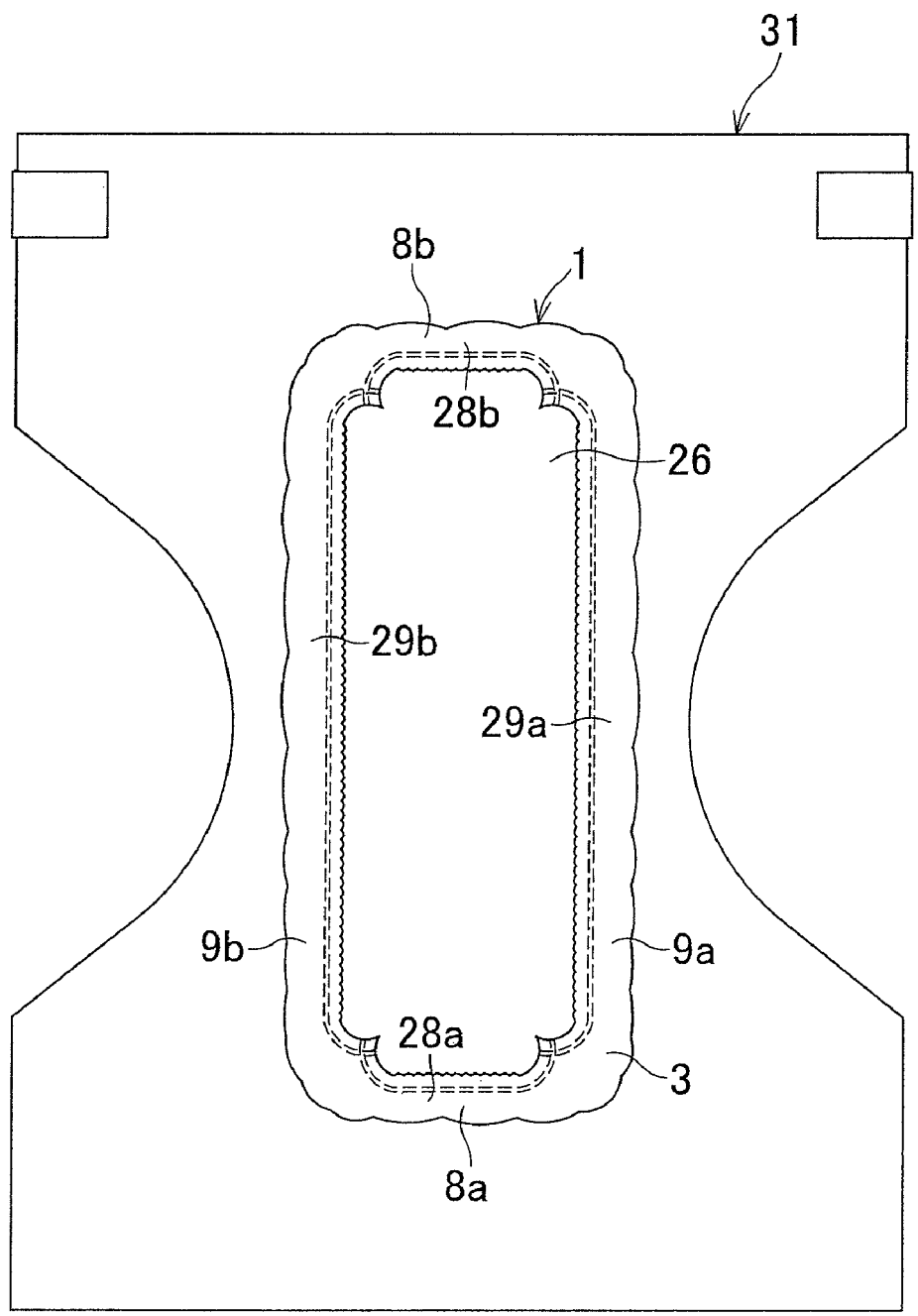
FIG. 3 is a diagram exemplarily illustrating a manner in which the body waste handling article is used.

FIG. 3 is a diagram exemplarily illustrating a manner in which the body waste handling article 1 is practically used. Referring to FIG. 3, the handling article 1 in its flattened state is placed on the inner surface of a disposable diaper 31 or a diaper cover in a crotch region thereof and the backsheet 3 of the handling article 1 is provided on its outer surface with attachment means such as pressure-sensitive adhesive, hot melt adhesive, hook or loop member constituting the so-called mechanical fastener (all not shown) by which the handling article 1 is temporarily or permanently attached to the crotch region. Of the handling article 1, the flaps 8a, 8b, 9a, 9b are folded back along the ends 22a, 22b and the lateral edges 23a, 23b of the core 16 to form leak-barrier peripheral walls 28a, 28b, 29a, 29b surrounding the handling article and these peripheral walls 28a, 28b, 29a, 29b and cooperating together to define an opening 26 (See FIG. 1) adapted to receive body waste such as feces and urine. So far as the diaper 31 is properly put on the wearer's body so that the wearer's anus and external genital lie within the opening 26, body waste can be reliably received by the handling article 1 and undesirable leakage of body waste from the handling article 1 can be reliably avoided. The handling article 1 used in this manner is preferably fixed to the diaper 31 only in a middle zone of the backsheet 3 as viewed in the transverse direction X as well as in the longitudinal direction Y in order to ensure that both the end flaps 8a, 8b and the lateral edges 9a, 9b are capable of being gathered without being affected by such fixation. While it is preferred to form the backsheet 3 by the liquid-impervious sheet to maintain the entire outer surface of the handling article 1 inclusive of the peripheral walls 28a, 28b, 29a, 29b in a liquid-impervious state, it is possible to use a liquid-pervious sheet as the backsheet 3 so far as such liquid-pervious sheet is used with the leak-barrier sheet 17. It is also possible to attach the handling article 1 constructed as has been described above to the inner side of cloth pants so as to be used as a urine-absorbent pad for incontinent patient.

Figure 4:
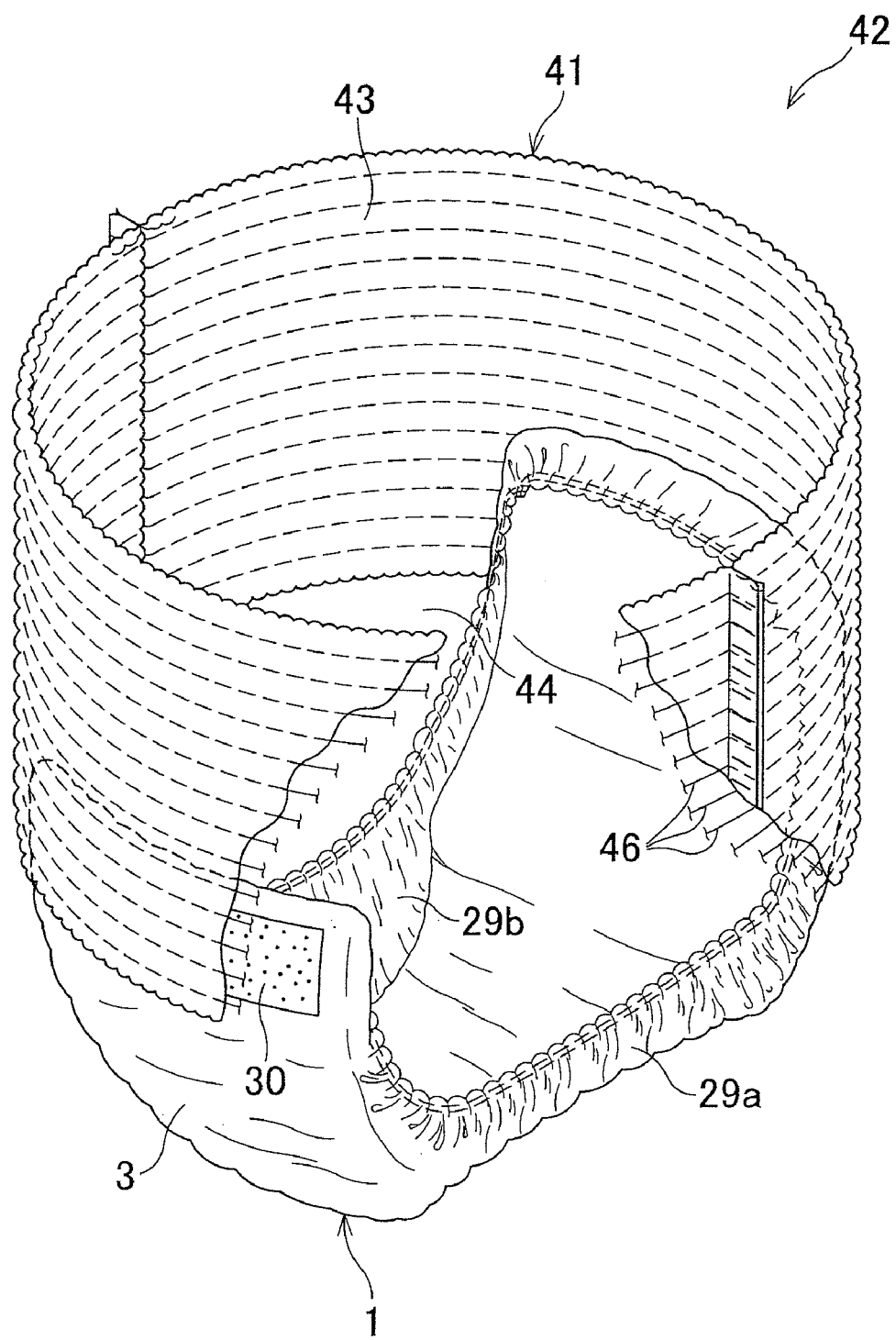
FIG. 4 is a diagram exemplarily illustrating a manner in which the body waste handling article is used.

FIG. 4 also is a diagram exemplarily illustrating a manner in which the body waste handling article 1 is practically used. In this example, the handling article 1 is temporarily or permanently attached to the inner surface of an annular belt-like member 41. More specifically, portions of the backsheet 3 extending in the vicinity of the ends 22a, 22b (See FIG. 2) of the core 16 are attached to the belt-like member 41 by attachment means 30 such as pressure-sensitive adhesive or hot melt adhesive so as to form a pants-type diaper 42. The belt-like member 41 defines a waist-opening 43 and cooperates with the handling article 1 to define a pair of leg-openings 44 also. The belt-like member 41 is provided with a plurality of elastic members 46 extending in a circumferential direction and attached in stretched state thereto.

Of the handling article 1, the topsheet 2 may be formed using material selected from the group including a liquid-pervious nonwoven fabric and a liquid-pervious plastic film. A suitable nonwoven fabric may be selected from the group including a spun bond nonwoven fabric, a melt bond nonwoven fabric and a laminate of these nonwoven fabric layers each having a basis weight in a range of 7 to 30 g/m$^2$. As an example of a suitable plastic film, a polyethylene film having a thickness in a range of 10 to 50 μm may be used. The backsheet may be preferably formed using material selected from the group including a substantially liquid-impervious nonwoven fabric, a liquid-impervious plastic film and a laminate consisting of a liquid-impervious or liquid-pervious nonwoven fabric and a liquid-impervious plastic film. As has previously been described, it is essential to use the leak-barrier sheet 17 with the backsheet 3 if the backsheet 3 is liquid-pervious. As stock material for the core 16, a water-absorbent material such as fluff pulp or a mixture of fluff pulp and super-absorbent polymer particles may be used. The preferred core 16 further comprises such water-absorbent material wrapped with tissue paper or nonwoven fabric having high water-absorbency and water-permeability and serving to improve shape retention and to facilitate the core 16 to be handled. While no particular planar shape of the core 16 is specified, the hourglass-shape as seen in FIG. 2 is advantageous since, on both sides of the middle of the handling article as viewed in the longitudinal direction Y, the peripheral walls 29a, 29b are defined, which adequately high to be easily deformable and kept in close contact with the crotch region of the wearer of the diaper 31 or 42 (See FIG. 1). Between the core 16 and the backsheet 3, the leak-barrier sheet 17 may be sandwiched, if it is required. As stock material for the leak-barrier sheet 17, a liquid-impervious plastic film such as a polyethylene film having a thickness in a range of 5 to 20 μm. Each of the elastic members 12a, 12b, 13a, 13b may be a rubber string having width and thickness in a range of 0.3 to 2 mm. While each of these elastic members 12a, 12b, 13a, 13b is paired so far as the illustrated embodiment is concerned, each of these elastic members may comprise a single rubber single or three or more rubber strings. These elastic members 12a, 12b, 13a, 13b may be selected to have appropriate tension so that the handling article 1 may have a shape as seen in FIG. 1. The handling article 1 shown by FIG. 2 as one of the preferred embodiments has a width of 160 mm and a length of 370 mm. In this embodiment, the topsheet 2 has a basis weight of 10 g/m$^2$ and formed from spun bond nonwoven fabric made of side-by-side type polyethylene/polypropylene composite fibers. The backsheet 3 is formed from a polyethylene film having a thickness of 20 μm and the core 16 is formed by fluff pulp having a basis weight of 200 g/m². Assumed that each of the flaps 8a, 8b, 9a, 9b has a width of at least 25 mm, strip-like test pieces each having a width of 20 mm×a length of 50 mm containing the elastic member 12a or 12b extending thereon along transversely middle zones thereof are cut away from the end flaps 8a, 8b in gathered state as shown in FIG. 1. Each of the test pieces is held at opposite ends over 5 mm, respectively, and stretched at a ratio of 150%. Preferred tension at this moment is in a range of 0.1 to 4.0 N. In the same manner, strip-like test pieces each having a width of 20 mm×a length of 50 mm containing the elastic member 13a or 13b extending thereon along transversely middle zones thereof are cut away from the lateral flaps 9a, 9b, respectively, and stretched at a ratio of 150%. Preferred tension at this moment is in a range of 0.1 to 4.0 N. In the case of the handling article of which the respective flaps 8a, 8b, 9a, 9b have the tension in question less than the range as has been described above, fit of these flaps 8a, 8b, 9a, 9b to the wearer's skin is inevitably deteriorated and sometimes a desired leak-barrier effect can not be expected. If the tension in question of these flaps 8a, 8b, 9a, 9b exceeds the above-mentioned range, on the contrary, constriction of these flaps 8a, 8b, 9a, 9b may cause the core 16 to get wrinkles. As a result, the effective area of the core 16 can not be utilized for absorption of body fluids, on one hand, and the flaps 8a, 8b, 9a, 9b uncomfortably irritate the wearer's skin, on the other hand. In the handling article 1, it is possible to provide a differential tension between the elastic members 12a and 12b and/or between the elastic members 13a and 13b so that the handling article 1 may have a shape differing from the shape as shown in FIG. 1 when the article 1 is constricted.

Figure 5:
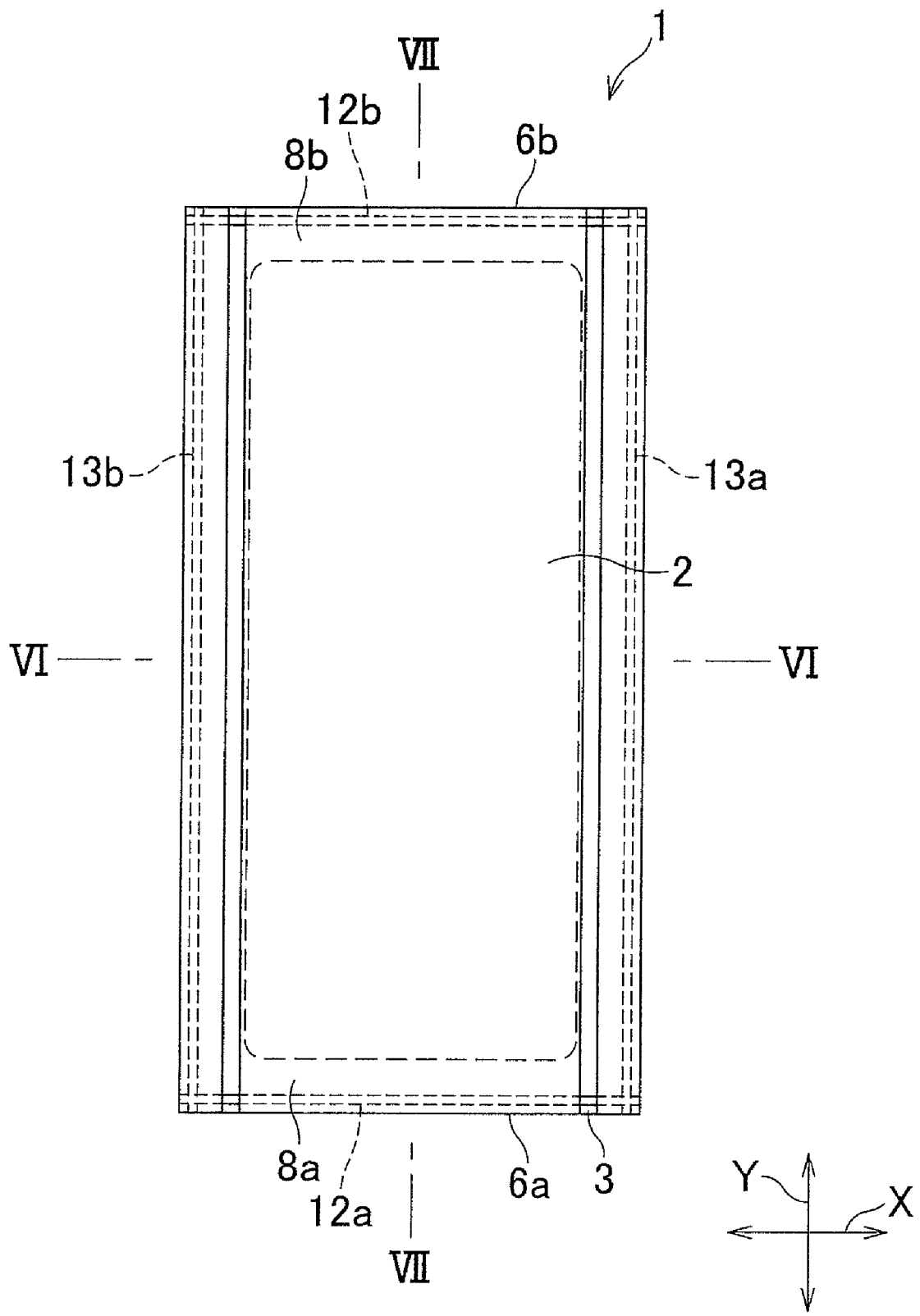
FIG. 5 is a view similar to FIG. 2, showing an alternative embodiment of the body waste handling article.
Figure 5:
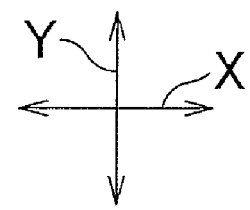
Figure 6:
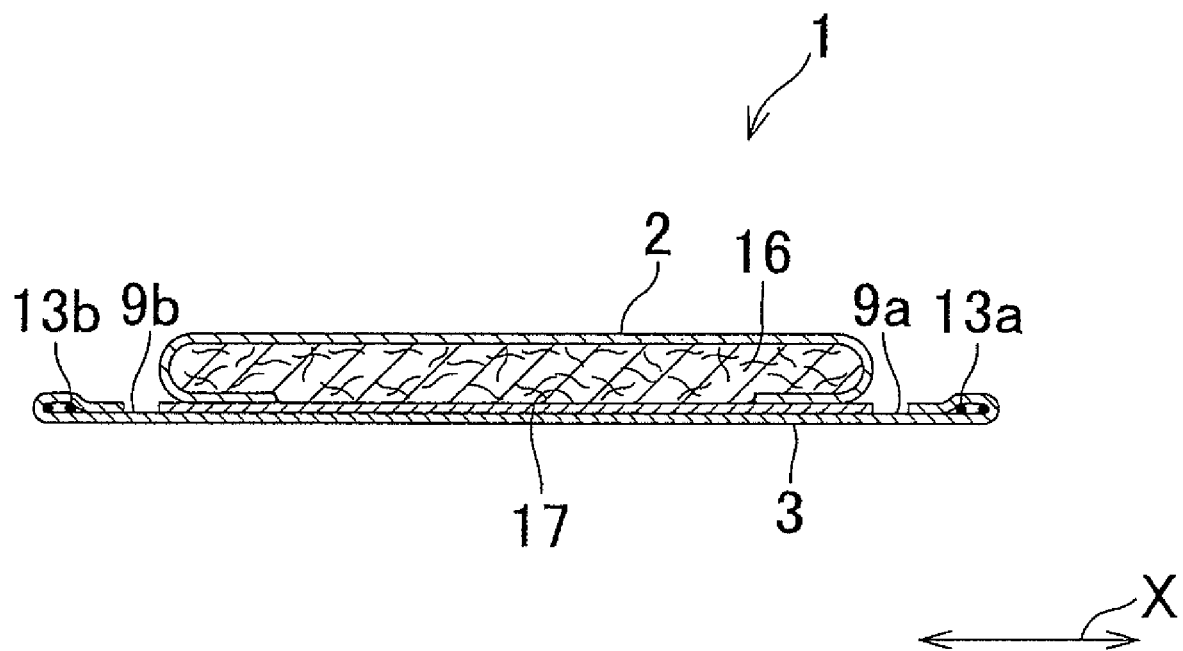
FIG. 6 is a sectional view taken along the line VI-VI in FIG. 5.
Figure 7:
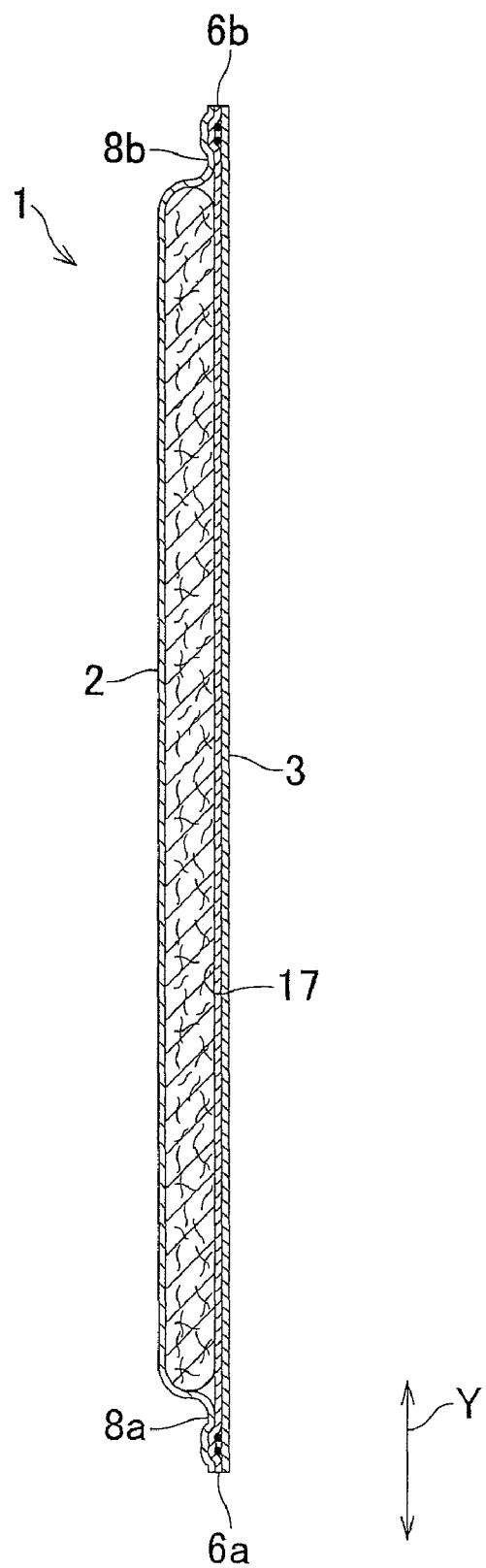
FIG. 7 is a sectional view taken along the line VII-VII in FIG. 5.

FIG. 5 is a view similar to FIG. 2, showing an alternative embodiment of the body waste handling article 1, FIG. 6 is a sectional view taken along the line VI-VI in FIG. 5 and FIG. 7 is a sectional view taken along the line VII-VII in FIG. 5. As will be apparent from FIG. 6, the topsheet 2 partially wraps the core 16 and the backsheet 3 laterally extends beyond the core 16. The leak-barrier sheet 17 is interposed between the topsheet 2 partially wrapping the core 16 and the backsheet 3. Portions of the backsheet 3 defining the lateral flaps 9a, 9b are folded back onto itself so as to sandwich the elastic members 13a, 13b, respectively. As will be apparent from FIG. 7, the topsheet 2, the backsheet 3 and the leak-barrier sheet 17 extend in the longitudinal direction Y of the handling article 1 to the respective ends 6a, 6b of the end flaps 8a, 8b. Under contraction of the elastic members 12a, 12b, 13a, 13b, the handling article 1 of FIG. 5 has a shape similar to the shape as seen in FIG. 1.

Figure 8:
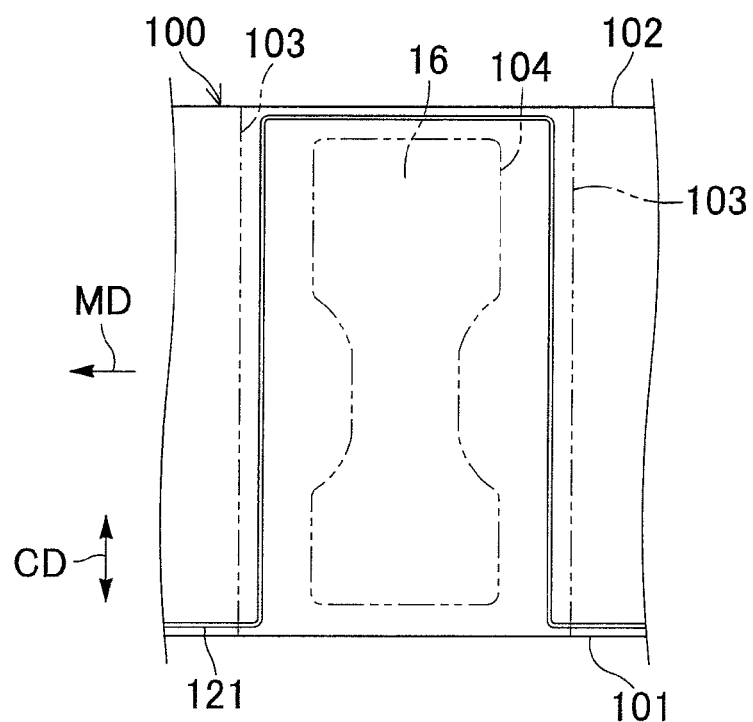
FIG. 8 is a schematic diagram illustrating a first example of the step for attachment of an elastic member.
Figure 9:
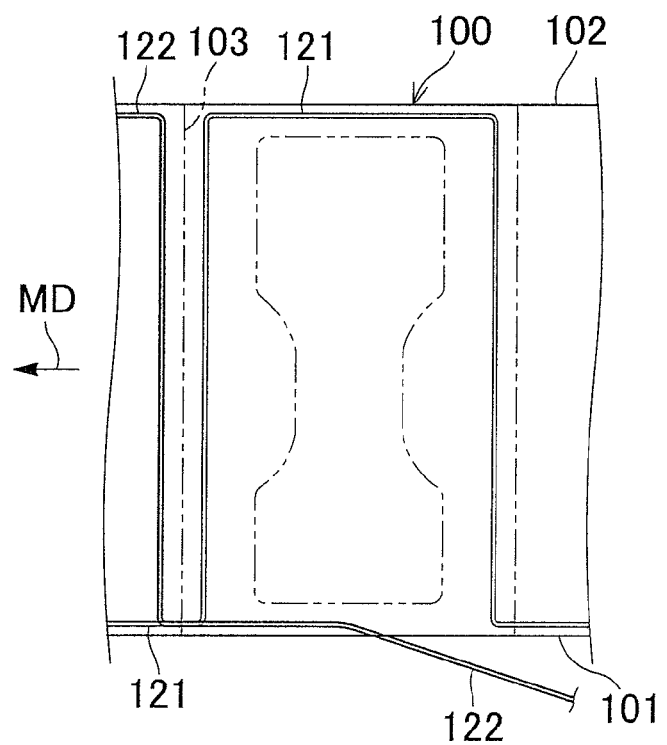
FIG. 9 is a schematic diagram illustrating the first example of the step for attachment of an elastic member.
Figure 10:
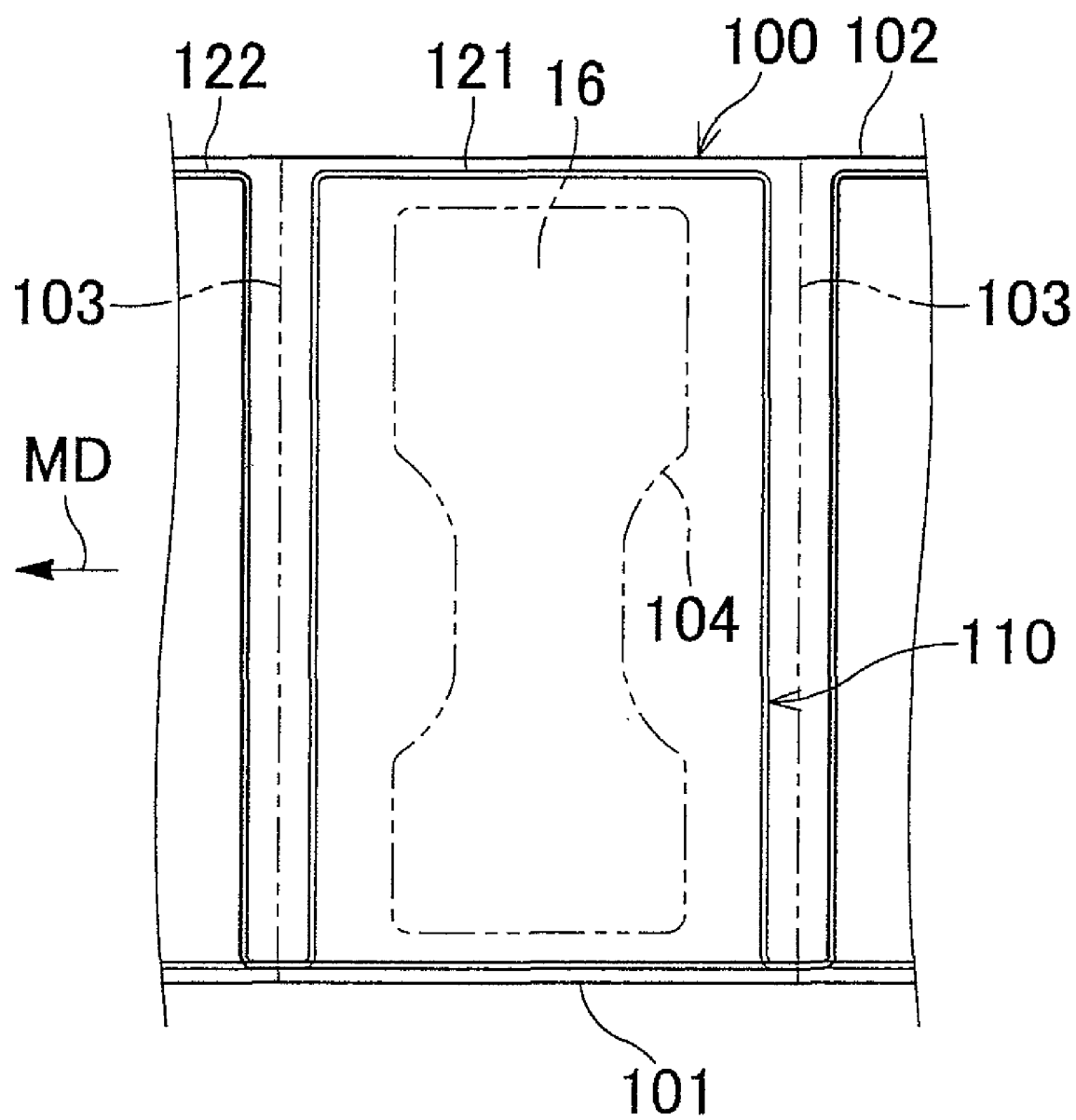
FIG. 10 is a schematic diagram illustrating the first example of the step for attachment of an elastic member.

FIGS. 8, 9 and 10 are schematic diagrams illustrating a first example of the step for attachment of the elastic members to the backsheet 3 so as to form a loop. In the case of the handling article 1 of FIG. 2, the elastic members 12a, 12b extending along the opposite ends of the article 1 and the elastic members 13a, 13b extending along the lateral edges of the article 1 are overlapped one to another at the corners of the backsheet 3 and substantially contiguous one to another. Compared to this, in the case of the handling article 1 of FIGS. 8, 9 and 10, these elastic members are attached to the backsheet 3 in a manner as follows. Referring first to FIG. 8, a nonwoven fabric web 100 used as the backsheet 3 continuously runs in the machine direction MD. The web 100 has a first edge 101 and a second edge 102 both extending in parallel to the machine direction MD. The web 100 is successively cut along first imaginary lines 103 arranged at regular intervals in the machine direction MD and extending in a cross direction CD orthogonal to the machine direction MD. In this way, the individual backsheets 3 are successively obtained. Between each pair of the adjacent first imaginary lines 103, a location at which the core 16 is to be laid is indicated by a secondary imaginary line 104. First paired elastic member 121 is continuously fed in a stretched state to the nonwoven fabric web 100 and attached thereto by means of hot melt adhesive (not shown) along a course extending in parallel to the first imaginary lines 103 and the second edge 102 and then making a substantially right-angled turn in the vicinity of points at which the first imaginary line 103 intersects with the first and second edges 101, 102. As illustrated, the first paired continuous elastic member 121 extends in parallel to the first edge 101.

Referring now to FIG. 9, second paired elastic member 122 is continuously fed in a stretched state to the nonwoven fabric web 100 being running in the machine direction MD. The second paired elastic member 122 is to the nonwoven fabric web 100 in parallel to the second edge 102 and the first imaginary line 103, then in parallel to the first edge 101. The second continuous elastic member 122 also makes a substantially right-angled turn in the vicinity of points at which the first imaginary line 103 intersects with the first and second edges 101, 102. Attachment of the first and second continuous elastic members 121, 122 to the web running in the machine direction MD in the manner as illustrated in FIGS. 8 and 9 is achieved by feeding the respective elastic members 121, 122 by the intermediary of an arm of the well known mechanism adapted to be reciprocated in the cross direction CD.

Referring finally to FIG. 10, the first and second continuous elastic members 121, 122 have been attached to the nonwoven fabric web 100 so as to surround the core 16 indicated by the imaginary line 104 and located between a pair of the adjacent first imaginary lines 103. In the vicinity of the points at which the first imaginary line 103 intersects with the first edge 101, the first paired continuous elastic member 121 and the second paired continuous elastic member 122 overlap each other so as to be made substantially contiguous to each other and to form a substantially rectangular loop 110 between each pair of the adjacent first imaginary lines 103. The nonwoven fabric web 100 having been provided with the elastic members in this manner may be successively cut along the first imaginary lines 103 to obtain the individual backsheets as shown by FIG. 2 in which the first and second continuous elastic members 121, 122 respectively become the elastic members 12a, 12b extending along the respective ends of the article 1 and the elastic members 13a, 13b extending along the lateral edges of the article 1. In this way, the handling article of a three-dimensional shape as shown in FIG. 1.

Figure 11:
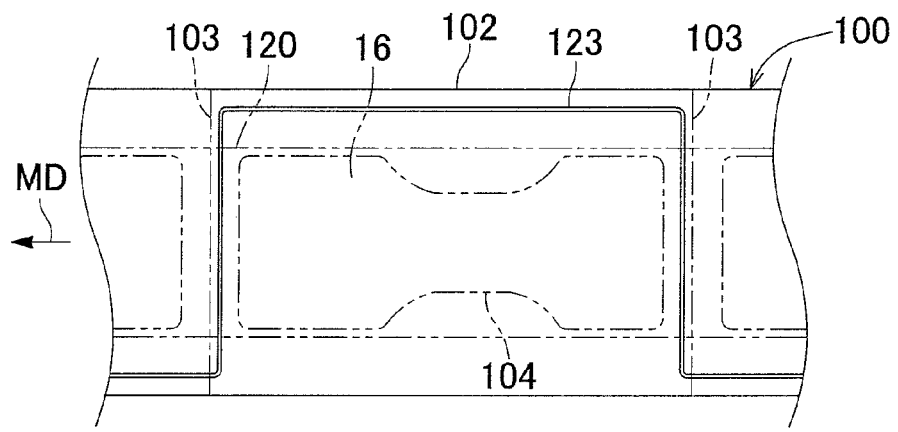
FIG. 11 is a schematic diagram illustrating a second example of the step for attachment of an elastic member.
Figure 12:
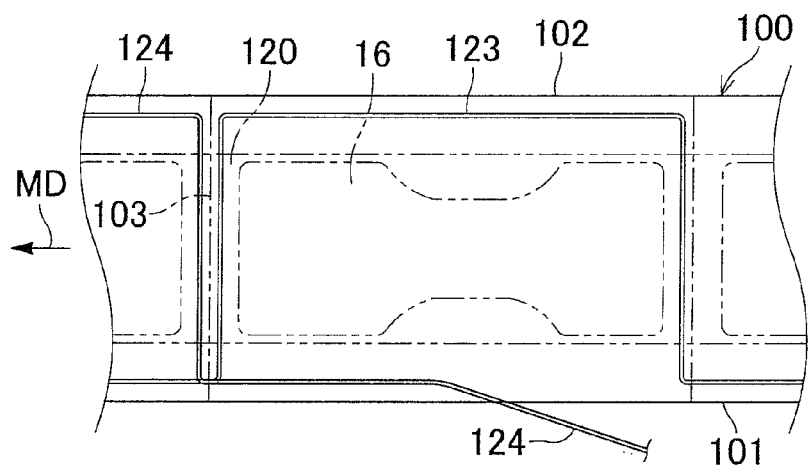
FIG. 12 is a schematic diagram illustrating the second example of the step for attachment of an elastic member.
Figure 13:
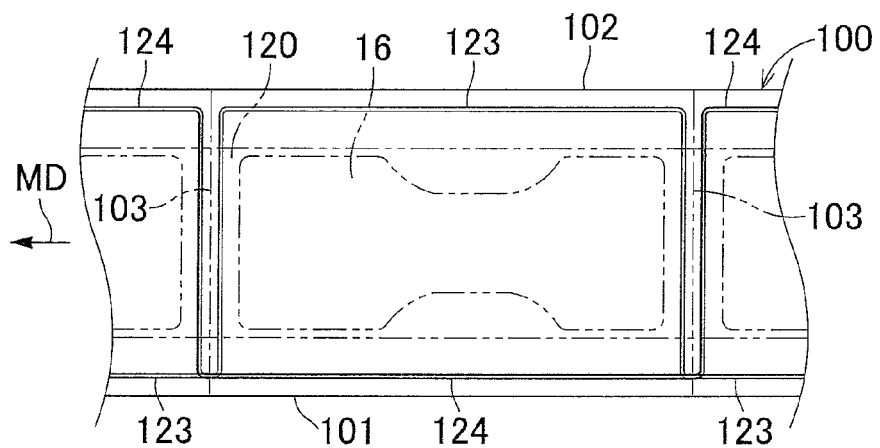
FIG. 13 is a schematic diagram illustrating the second example of the step for attachment of an elastic member.

FIGS. 11, 12 and 13 are schematic diagrams illustrating a second example of the step for attachment of elastic members to the backsheet 3 so as to form a loop. A process illustrated in FIGS. 11, 12 and 13 is distinguished from the process as illustrated in FIGS. 8, 9 and 10 in that the hourglass-shaped core 16 indicated by the imaginary line heads for in the machine direction MD with respect to the nonwoven fabric web 100 continuously running in the machine direction MD and this core 16 is covered with a liquid-pervious nonwoven fabric web 120 indicated by imaginary line. Referring to FIG. 11, a third continuous elastic member 123 is attached to the nonwoven fabric web 100 so as to extend in parallel to each pair of the adjacent first imaginary lines 103 and to the second edge 102 of the nonwoven fabric web 100.

Referring to FIG. 12, a fourth continuous elastic member 124 is attached to the nonwoven fabric web 100 so as to extend in parallel to the second edge 102 and the first imaginary line 103 and thereafter so as to extend in parallel to the first edge 101.

Referring finally to FIG. 13, the nonwoven fabric web 100 having the third and fourth continuous elastic members 123, 124 attached thereto are folded back along the first edge 101 and the second edge 102 to wrap the third and fourth continuous elastic members 123, 124 extending along these edges 101, 102. Then the nonwoven fabric web 100 may be successively cut along the first imaginary lines 103 to obtain the handling article similar to that as shown in FIG. 2. The third and fourth continuous elastic members 123, 124 respectively become the elastic members 12a, 12b extending along the respective ends of the article 1 and the elastic members 13a, 13b extending along the lateral edges of the article 1 in FIG. 2. The core 16 and the liquid-pervious nonwoven fabric 120 wrapping the core 16 respectively correspond to the core 16 and the topsheet 2 in FIG. 2.

The present invention provides the body waste handling article having a construction sufficiently simplified to facilitate production thereof.

The entire discloses of Japanese Patent application No. 2006-174443 filed on Jun. 23, 2006 including specification, drawings and abstract are herein incorporated by reference in its entirety.

What is claimed is:

1. A disposable body waste handling article, comprising:
   a first sheet defining a liquid-pervious skin-contactable surface;
   a body fluid absorbent core having a peripheral edge;
   a second sheet extending outward beyond said peripheral edge of said core and contoured by
   a pair of lateral edges extending in a longitudinal direction of the article and
   a pair of ends extending in a transverse direction of the article; and
   a liquid-impervious leak-barrier sheet sandwiched between said core and said second sheet,
wherein said second sheet includes
   lateral flaps between respective said lateral edges and the peripheral edge of the absorbent core, and end flaps between respective said ends and the peripheral of the absorbent core; and
   elastic members extending along and attached in a stretched state to said lateral flaps and said end flaps;
wherein
   said core is sandwiched between the first sheet and the second sheet;
   said elastic members directly overlap one upon another and cooperate one with another to define a closed loop; and
   contraction of said elastic members constricts said lateral flaps and said end flaps in said longitudinal direction as well as in said transverse direction so as to narrow said loop and causes said lateral flaps and said end flaps to be folded back along the peripheral edge of said core toward said skin-contactable surface,
wherein said elastic members comprise
   a first elastic member continuously extending along said lateral edges and one of said ends and
   a second elastic member extending along the other of said ends,
   wherein first and second elastic members directly overlap one upon another in vicinities of intersections of said lateral edges and said other end and thereby substantially contiguous one to another.

2. The article according to claim 1, wherein said second sheet has
   an inner side facing said core, and
   an outer side facing away from said core and adapted to be attached to an inner surface of a diaper or a diaper cover in a crotch region thereof.

3. The article according to claim 1, wherein said second sheet is liquid-impervious.

4. A pants-type wearing diaper, comprising:
   a disposable body waste handling article; and
   a belt member defining an annulus which is elastically stretchable and contractible in a circumferential direction of the diaper,
wherein
said article is attached to said belt member at said end flaps, and
said article includes
   a first sheet defining a liquid-pervious skin-contactable surface;
   a body fluid absorbent core having a peripheral edge;
   a second sheet extending outward beyond said peripheral edge of said core and contoured by
a pair of lateral edges extending in a longitudinal direction of the article and a pair of ends extending in a transverse direction of the article,
wherein said second sheet includes
   lateral flaps between respective said lateral edges and the peripheral edge of the absorbent core, and end flaps between respective said ends and the peripheral of the absorbent core; and
   elastic members extending along and attached in a stretched state to said lateral flaps and said end flaps;
wherein
   said core is sandwiched between the first sheet and the second sheet;
   said elastic members directly overlap one upon another and cooperate one with another to define a closed loop; and
   contraction of said elastic members constricts said lateral flaps and said end flaps in said longitudinal direction as well as in said transverse direction so as to narrow said loop and causes said lateral flaps and said end flaps to be folded back along the peripheral edge of said core toward said skin-contactable surface,
   wherein said elastic members comprise
   a first elastic member continuously extending along said lateral edges and one of said ends and
   a second elastic member extending along the other of said ends,
   wherein first and second elastic members directly overlap one upon another in vicinities of intersections of said lateral edges and said other end and thereby substantially contiguous one to another.

* * * * *